(12) United States Patent
Jensen

(10) Patent No.: US 10,285,606 B2
(45) Date of Patent: May 14, 2019

(54) METHODS AND APPARATUS FOR THE ON-LINE AND REAL TIME ACQUISITION AND ANALYSIS OF VOLTAGE PLETHYSMOGRAPHY, ELECTROCARDIOGRAM AND ELECTROENCEPHALOGRAM FOR THE ESTIMATION OF STROKE VOLUME, CARDIAC OUTPUT, AND SYSTEMIC INFLAMMATION

(71) Applicant: QUANTIUM MEDICAL S.L., Barcelona (ES)

(72) Inventor: Erik Weber Jensen, Barcelona (ES)

(73) Assignee: QUANTIUM MEDICAL S.L. (ES)

( * ) Notice: Subject to any disclaimer, the term of this patent is extended or adjusted under 35 U.S.C. 154(b) by 193 days.

(21) Appl. No.: 15/102,961

(22) PCT Filed: Dec. 15, 2014

(86) PCT No.: PCT/DK2014/000061
§ 371 (c)(1),
(2) Date: Jun. 9, 2016

(87) PCT Pub. No.: WO2015/086020
PCT Pub. Date: Jun. 18, 2015

(65) Prior Publication Data
US 2016/0374581 A1 Dec. 29, 2016

(30) Foreign Application Priority Data
Dec. 13, 2013 (DK) .................................. 2013 00689

(51) Int. Cl.
*A61B 5/02* (2006.01)
*A61B 5/04* (2006.01)
(Continued)

(52) U.S. Cl.
CPC ........ *A61B 5/04012* (2013.01); *A61B 5/0205* (2013.01); *A61B 5/0245* (2013.01);
(Continued)

(58) Field of Classification Search
CPC . A61B 5/04012; A61B 5/0205; A61B 5/0476; A61B 5/7264; A61B 5/0245; A61B 5/02405; A61B 5/0295
See application file for complete search history.

(56) References Cited

U.S. PATENT DOCUMENTS

| 3,340,867 A | 9/1967 | Kubicek et al. |
| 3,835,840 A | 9/1974 | Mount |

(Continued)

FOREIGN PATENT DOCUMENTS

| WO | 2012/092303 A1 | 7/2012 |
| WO | WO 2012/122637 | 9/2012 |

(Continued)

OTHER PUBLICATIONS

J.M. Huston et al., The Pulse of Inflammation: Heart Rate Variability, The Cholinergic Anti-Inflammatory Pathway, and Implications for Therapy, Journal of Internal Medicine, Jan. 2011, 269(1), 45-53.
(Continued)

*Primary Examiner* — Rex R Holmes
(74) *Attorney, Agent, or Firm* — Cook Alex Ltd.

(57) ABSTRACT

Apparatus for determining stroke volume, cardiac output and systemic inflammation by fuzzy logic combination of features extracted from a voltage measured over the thorax, electrocardiogram and electroencephalogram comprising a) sensor for measuring electroencephalogram; b) sensor for measuring the electrocardiogram; c) calculating the heart rate variability from the electrocardiogram; d) two electrodes (1, 2) for measuring the voltage generated by a constant current generator in two other electrodes (1, 2); e)
(Continued)

Figure 1:
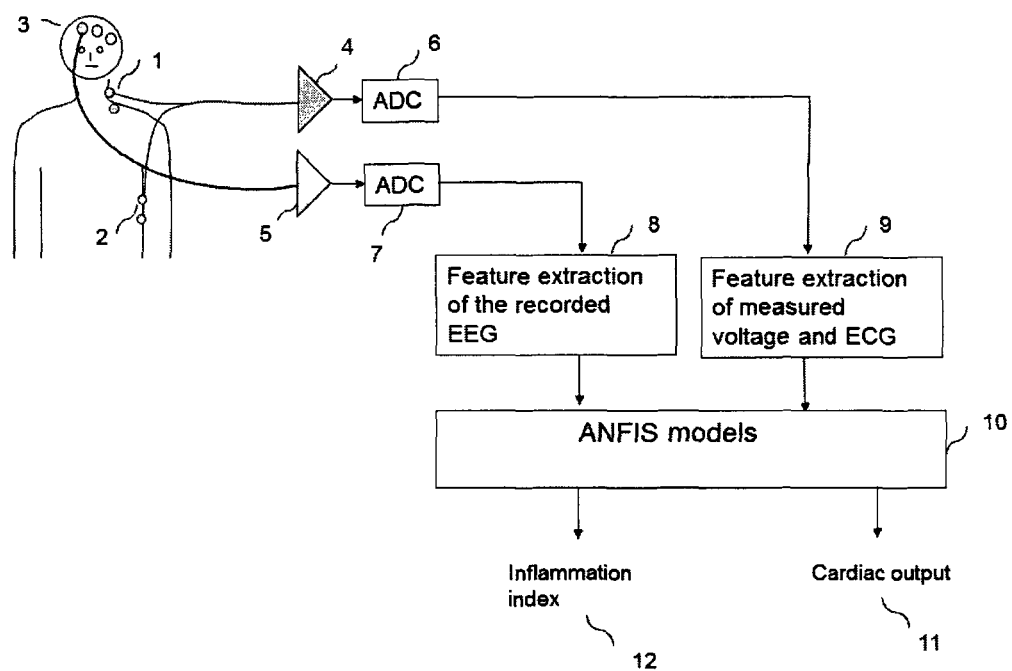

calculating the area under the curve of voltage for each heart-beat; f) calculating the derivative of the voltage curve; g) calculating the transfer entropy between EEG and ECG; h) combining at least 3 extracted parameters using an Adaptive Neuro Fuzzy inference system (ANFIS) or any other fuzzy reasoner into a final index of cardiac output; i) combining at least 3 extracted parameters using an Adaptive Neuro Fuzzy Inference System or any other fuzzy reasoner into a final index of systemic inflammation.

13 Claims, 10 Drawing Sheets

(51) Int. Cl.
| | |
|---|---|
| *A61B 5/00* | (2006.01) |
| *A61B 5/024* | (2006.01) |
| *A61B 5/0245* | (2006.01) |
| *A61B 5/0295* | (2006.01) |
| *A61B 5/0476* | (2006.01) |
| *A61B 5/0205* | (2006.01) |
| *G16H 40/63* | (2018.01) |
| *G16H 50/30* | (2018.01) |
| *G16H 50/20* | (2018.01) |

(52) U.S. Cl.
CPC ........ *A61B 5/0295* (2013.01); *A61B 5/02405* (2013.01); *A61B 5/0476* (2013.01); *A61B 5/7264* (2013.01); *G16H 40/63* (2018.01); *G16H 50/20* (2018.01); *G16H 50/30* (2018.01)

(56) References Cited

U.S. PATENT DOCUMENTS

| | | |
|---|---|---|
| 4,450,527 A | 5/1984 | Sramek |
| 6,572,542 B1 | 6/2003 | Houben et al. |
| 7,941,199 B2 | 5/2011 | Kiani |
| 2005/0137484 A1 | 6/2005 | Griffin et al. |
| 2007/0260147 A1 | 11/2007 | Giftakis et al. |
| 2008/0013747 A1 | 1/2008 | Tran |
| 2010/0280372 A1 | 11/2010 | Poolman et al. |
| 2011/0040713 A1 | 2/2011 | Colman et al. |
| 2011/0137852 A1 | 6/2011 | Gajic et al. |
| 2011/0190601 A1 | 8/2011 | Osypka et al. |

FOREIGN PATENT DOCUMENTS

| | | |
|---|---|---|
| WO | WO 2013/183001 | 12/2013 |
| WO | 2015/086020 A1 | 6/2015 |

OTHER PUBLICATIONS

E.W. Jensen et al., Monitoring Hypnotic Effect and Nociception With Two EEG-Derived Indices, qCON and qNOX, During General Anaesthesia, Acta Anaesthesiologica Scandinavica, Sep. 2014, 58(8), 933-941.
K.J. Tracey, Understanding Immunity Requires More Than Immunology, Nature Immunology, 2010, 11, 561-564.
R. Vicente et al., Transfer Entropy—A Model-Free Measure of Effective Connectivity for the Neurosciences, Journal of Computational Neuroscience, 2011, 30, 45-67.
International Search Report of PCT/DK2014/000061, dated Mar. 19, 2015.
Written Opinion of the International Search Authority of PCT/DK2014/000061, dated Mar. 19, 2015.
European Patent Office, extended European search report, counterpart EP Appl No. 14868969.8, 27 pages (dated Sep. 3, 2018).
Petkovic, D. et al., "Adaptive neuro fuzzy selection of heart rate variability parameters affected by autonomic nervous system", Expert Systems with Applications, vol. 40, No. 11, pp. 4490-4495, (Sep. 1, 2013).
No Author, "Heart rate variability—Wikipedia", retrieved from the Internet, 12 pages, (Oct. 31, 2013).
Chen, W-L. et al., "Characteristics of Heart Rate Variability Can Predict Impending Septic Shock in Emergency Department Patients with Sepsis", Academic Emergency Medicine, vol. 14, No. 5, pp. 392-397 (Mar. 26, 2007).

First derivative of Voltage $\frac{dV}{dt}$

Figura 9

METHODS AND APPARATUS FOR THE ON-LINE AND REAL TIME ACQUISITION AND ANALYSIS OF VOLTAGE PLETHYSMOGRAPHY, ELECTROCARDIOGRAM AND ELECTROENCEPHALOGRAM FOR THE ESTIMATION OF STROKE VOLUME, CARDIAC OUTPUT, AND SYSTEMIC INFLAMMATION

CROSS-REFERENCE TO RELATED APPLICATIONS

The present application is a U.S. national stage application of International Patent Application No. PCT/DK2014/000061, filed Dec. 15, 2014, which claims the benefit of and priority to Danish Patent Application No. PA 2013300389, filed Dec. 13, 2013, both of which are incorporated by reference herein in their entireties.

INTRODUCTION

As the patient's haemodynamic status may change rapidly, continuous monitoring of cardiac output will provide information allowing rapid adjustment of therapy. For more than three decades the pulmonary artery catheter (PAC) thermodilution method has been generally accepted and is still the clinical standard to which all other methods are compared.

The reference method for monitoring cardiac output (CO) is the pulmonary artery catheter (PAC). The PAC is also, termed a Swan-Ganz catheter, named after the inventors of the technique. The PAC is introduced into vena cava, and then fed through the heart and the tip of the catheter is positioned in the pulmonary arthery.

The long history of use has led to much experience with its technology, clinical application and inadequacies. Over the years, many new methods attempted to replace the thermodilution technique, both invasive and non-invasive methods.

The bio-impedance method was introduced, five decades ago, as a simple, low-cost method that gives information about the cardiovascular system and/or (de)-hydration status of the body in a non-invasive way. To improve the related thoracic impedance method, over the years, a diversity of thoracic impedance measurement systems appeared. These systems determine stroke volume (SV) or CO on a beat-to-beat time base. More than 150 validation studies have been reported, with different results compared to a reference method. The accuracy of this technique is increased (along with its invasiveness) when the electrodes are placed directly in the left ventricle, rather than on the chest. Alternatively, the accuracy can be improved by applying advanced signal processing or combining several parameters into a final estimate of the cardiac output.

BACKGROUND

The present invention uses injection of a constant current at which the voltage is measured. However, as the current is constant measuring the voltage is proportional to the impedance, hence the concept of bio-impedance will be described in the following section.

Bioimpedance measurement on body parts was originally described in the U.S. Pat. No. 3,340,867, by Kubicek, patented Sep. 12, 1967. This invention describes impedance plethysmography, in particularly useful for determining cardiac output. The claims include position of electrodes being upper and lower part of the thorax. Later, bioimpedance measurement on body parts was described in the U.S. Pat. No. 3,835,840, Impedance plethysmography, apparatus and methods, priority date Sep. 27, 1973. This patent describes a method for using the electrical impedance as a correlate to blood flow in aorta or other arteries.

Sramek filed Jun. 29, 1982, the patent, Noninvasive Continuous Cardiac Outputmonitor, U.S. Pat. No. 4,450,527, where a modification of the original Nyboer equation has been made.

Combination of Parameters.

The device uses ANFIS models to combine the parameters, for the definition of the stroke volume, cardiac output and the inflammation index.

The parameters extracted from the two sensors and the demographic data of the patient are used as input to an Adaptive Neuro Fuzzy Inference System (ANFIS).

Overview of ANFIS

ANFIS is a hybrid between a fuzzy logic system and a neural network, it does not assume any mathematical function governing the relationship between input and output. ANFIS applies a data driven approach where the training data decides the behaviour of the system.

Figure 6:
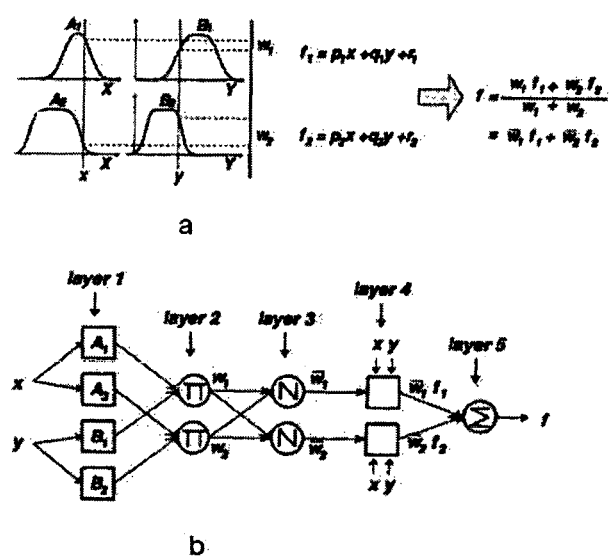

The five layers of ANFIS, shown in FIG. 6, have the following functions:

Each unit in Layer 1 stores three parameters to define a bell-shaped membership function. Each unit is connected to exactly one input unit and computes the membership degree of the input value obtained.

Each rule is represented by one unit in Layer 2. Each unit is connected to those units in the previous layer, which are from the antecedent of the rule. The inputs into a unit are degrees of membership, which are multiplied to determine the degree of fulfillment for the rule represented.

In Layer 3, for each rule there is a unit that computes its relative degree of fulfillment by means of a normalisation equation. Each unit is connected to all the rule units in Layer 2.

The units of Layer 4 are connected to all input units and to exactly one unit in Layer 3. Each unit computes the output of a rule.

An output unit in Layer 5 computes the final output by summing all the outputs from Layer 4.

Standard learning procedures from neural network theory are applied in ANFIS. Back-propagation is used to learn the antecedent parameters, i.e. the membership functions, and least squares estimation is used to determine the coefficients of the linear combinations in the rules' consequents. A step in the learning procedure has two passes. In the first pass, the forward pass, the input patterns are propagated, and the optimal consequent parameters are estimated by an iterative least mean squares procedure, while the antecedent parameters are fixed for the current cycle through the training set. In the second pass, the backward pass, the patterns are propagated again, and in this pass back-propagation is used to modify the antecedent parameters, while the consequent parameters remain fixed. This procedure is then iterated through the desired number of epochs. If the antecedent parameters initially are chosen appropriately, based on expert knowledge, one epoch is often sufficient as the LMS algorithm determines the optimal consequent parameters in one pass and if the antecedents do not change significantly by use of the gradient descent method, neither will the LMS calculation of the consequents lead to another result. For example in a 2-input, 2-rule system, rule 1 is defined by if $x$ is $A$ and $y$ is $B$ then $f_1 = p_1 x + q_1 y + r_1$ where p, q and r are linear, termed consequent parameters or only consequents. Most common is f of first order as higher order Sugeno fuzzy models introduce great complexity with little obvious merit.

Number of Classes.

The inputs to the ANFIS system are fuzzified into a number of predetermined classes. The number of classes should be larger or equal two. The number of classes can be determined by different methods. In traditional fuzzy logic the classes are defined by an expert. The method can only be applied if it is evident to the expert where the landmarks between two classes can be placed. ANFIS optimizes the position of the landmarks, however the gradient descent method will reach its minimum faster if the initial value of the parameters defining the classes is close to the optimal values. By default, ANFIS initial landmarks are chosen by dividing the interval from minimum to maximum of all data into n equidistant intervals, where n is the number of classes. The number of classes could also be chosen by plotting the data in a histogram and visually deciding for an adequate number of classes, by ranking as done by FIR, through various clustering methods or Markov models. The ANFIS default was chosen for this invention and it showed that more than 3 classes resulted in instabilities during the validation phase, hence either 2 or 3 classes were used.

Number of Inputs.

Both the number of classes and number of inputs add to the complexity of the model i.e. the number of parameters. For example, a system with 4 inputs, each fuzzified into 3 classes consists of 36 antecedent (non-linear) and 405 consequent (linear) parameters, calculated by the following two formulas:

$$\text{antecedents} = \text{number of classes} \times \text{number of inputs} \times 3$$

$$\text{consequents} = \text{number of classes}^{\text{number of inputs}} \times (\text{number of inputs} + 1)$$

The number of input-output pairs should in general be much larger, (at least a factor 10) than the number of parameters in order to obtain a meaningful solution of the parameters.

Stability Criteria.

Unfortunately there exists no definition of stability criteria for neuro-fuzzy systems. The most useful tool for ensuring stability is the experience obtained by working with a certain neuro-fuzzy system such as ANFIS in the context of a particular data set, and testing with extreme data for example obtained by simulation Number of Epochs.

ANFIS uses a Root Mean Square Error (RMSE) to validate the training result and from a set of validation data the RMSE validation error can be calculated after each training epoch. One epoch is defined as one update of both the antecedent and the consequent parameters. An increased number of epochs will in general decrease the training error.

Other Terms.

The term "electroencephalography (EEG)" refers hereinafter to the recording of electrical activity along the scalp. EEG measures voltage fluctuations resulting from ionic current flows within the neurons of the brain. In clinical contexts, EEG refers to the recording of the brain's spontaneous electrical activity as recorded from multiple electrodes placed on the scalp. Diagnostic applications generally focus on the spectral content of EEG, that is, the type of neural oscillations that can be observed in EEG signals.

The term "electromyography (EMG)" refers hereinafter to a technique for evaluating and recording the electrical activity produced by skeletal muscles. EMG is performed using an instrument called an electromyograph, to produce a record called an electromyogram. An electromyograph detects the electrical potential generated by muscle cells when these cells are electrically or neurologically activated. The signals can be analyzed to detect medical abnormalities, activation level, or recruitment order or to analyze the biomechanics of human or animal movement.

The term "qCON" refers to an index of hypnotic effect derived from the EEG. The EEG is recorded from frontal electrodes (FIG. 1) (3), amplified (5) and digitized (7). Features are extracted from the EEG (8) from which the qCON is calculated. The qCON is defined as a scale from 0 to 99, where 80-99 indicates awake, 60-80 sedations, 40-60 adequate depth of anaesthesia and 0 to 40 deep anaesthesia. The qCON is further described in the article: Jensen E W, Valencia J F, López A, Anglada T, Ramos Y, Serra R, Jospin M, Pineda P, Gambus P Monitoring hypnotic effect and nociception with two EEG derived indices, qCON and qNOX, during general anaesthesia. Acta Anaesthesiol Scand. 2014 September; 58(8):933-41

The term "electrocardiography (ECG)" refers hereinafter to is a transthoracic (across the thorax or chest) interpretation of the electrical activity of the heart over a period of time, as detected by electrodes attached to the surface of the skin and recorded by a device external to the body. The recording produced by this noninvasive procedure is termed an electrocardiogram. An ECG picks up electrical impulses generated by the depolarization of cardiac tissue and translates into a waveform. The waveform is then used to measure the rate and regularity of heartbeats, as well as the size and position of the chambers, the presence of any damage to the heart, and the effects of drugs or devices used to regulate the heart, such as a pacemaker.

The term "fast Fourier transform (FFT)" refers hereinafter to an algorithm to compute the discrete Fourier transform (DFT) and its inverse. A Fourier transform converts time (or space) to frequency and vice versa; an FFT rapidly computes such transformations. As a result, fast Fourier transforms are widely used for many applications in engineering, science, and mathematics.

The term "RR intervals" refer to the time between successive R-peaks in the ECG. From the RR intervals the following parameters are extracted, as shown in table 1. These are calculated by the device. NNi refers to the ith RR interval.

TABLE 1

Time and frequency domain variables.

| Variable | Description |
| --- | --- |
| HR (bpm) | Heart rate, reciprocate of the mean of all RR intervals |
| RMSSD (ms) | Root mean square differences between successive RR intervals |

$$\text{RMSSD} = \sqrt{\frac{1}{NN} \sum_i (NN_i - NN_{i-1})^2}$$

| | |
| --- | --- |
| SDSD (ms) | Standard deviation of differences between successive RR intervals |
| pNN50 (%) | Number of interval differences of successive RR intervals greater than 50 ms divided by the total number of RR intervals., i.e: if $(NN_i - NN_{i-1}) > 50$ ms, count ++; count/n * 100; |

TABLE 1-continued

Time and frequency domain variables.

| Variable | Description |
| --- | --- |
| HF (ms$^2$) | Power in high frequency range (0.15-0.4 Hz) |
| HFn (n.u) | HF power in normalized units, HFn = HF/(LF + HF) * 100 |
| LF | Power in low frequency range (0-0.14 Hz) |

Detailed Description of the Invention for Monitoring Cardiac Output.

The novelty of this patent is the combination of several parameters extracted from the voltage plethysmographic curve and the heart rate variability. The voltage plethysmographic curve is achieved by applying a constant current of 400 uA between the upper and lowest electrodes on the thorax, see FIG. 1, (1) and (2). The voltage plethysmographic curve is also referred to as the voltage plethysmogram (VP) or the voltage curve. The voltage curves are achieved for each heart beat, consecutive curves have normally a similar morphology. The voltage is measured between the electrodes adjacent to upper and lowest electrodes (inner electrodes). The current will seek the path with the lowest impedance, i.e. the blood filled aorta. Hence the more blood present the impedance will be lower and consequently the voltage as well. The voltage curve and the ECG are recorded from the same electrodes (1) (2), amplified (4), digitized (6). Features are extracted from the voltage curve and the ECG (9), those features are fed into ANFIS models (11) where the output is cardiac output (11) and the final inflammation index (12).

The voltage plethysmography of each heart-beat is a correlate to the stroke volume (SV). The voltage plethysmogram (VP) will show periodic fluctuations from which the heart rate (HR) can be detected. The HR could also be detected from the ECG and the two compared to assure correct performance. From SV and HR the cardiac output (CO) can be computed by $$CO = HR \times SV.$$

Figure 2:
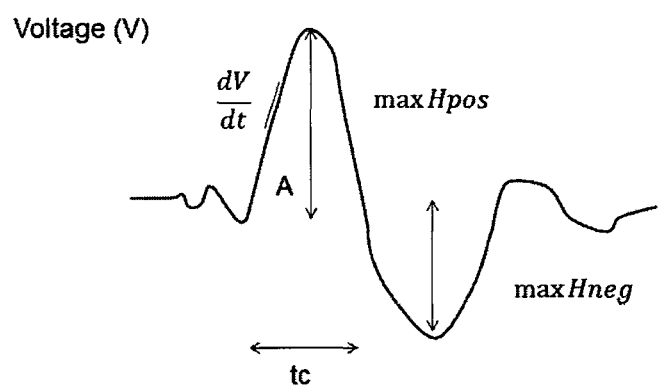

FIG. 2 shows a typical example of the voltage curve. The variable, $t_c$, is the opening time of the aortic valve. The area, A, is an initial correlate of the SV. A is calculated by integrating the voltage plethysmogram over the period $t_c$. The start time of $t_c$ is defined as an increase in the VP in the 5-15% range while the ending time of $t_c$ is defined as the start of the interval where the VP is stable within changes of 1-5%.

The maximum positive amplitude and the maximum negative amplitude is assessed from the voltage curve. The maximum positive amplitude of the voltage curve (maxHpos) and the (maxHneg) is shown in FIG. 2. Additionally the derivative of the VP is calculated. The maximum of the derivative is termed $$\max\left(\frac{dV}{dt}\right)$$

and used as an input to the ANFIS1 model. From the dV/dt curve the left ventricular ejection time (LVET) can be estimated as time from 20-30% after the dv/dt starts to increase (B, on FIG. 3) until the minimum of dv/dt (X, on FIG. 3) within the period (RR interval).

Figure 3:
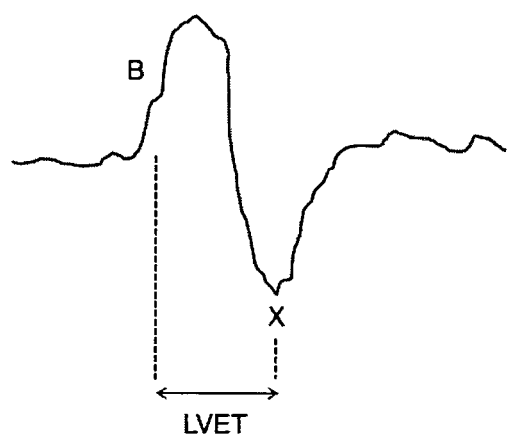
Figure 4:
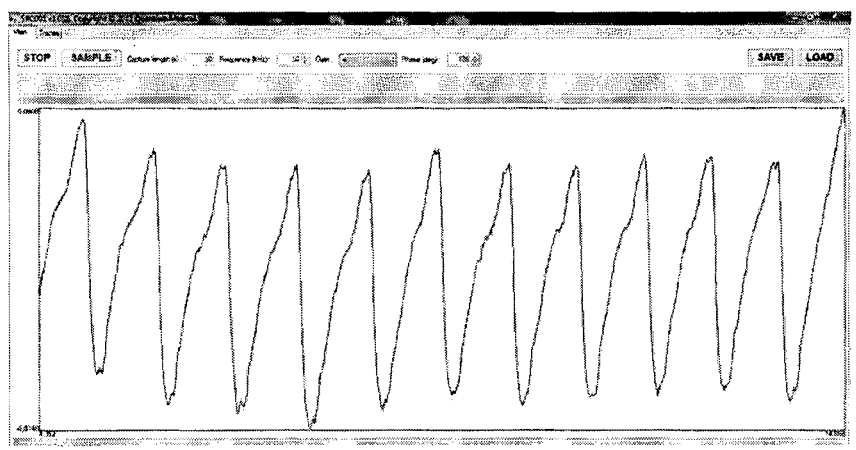
Figure 5:
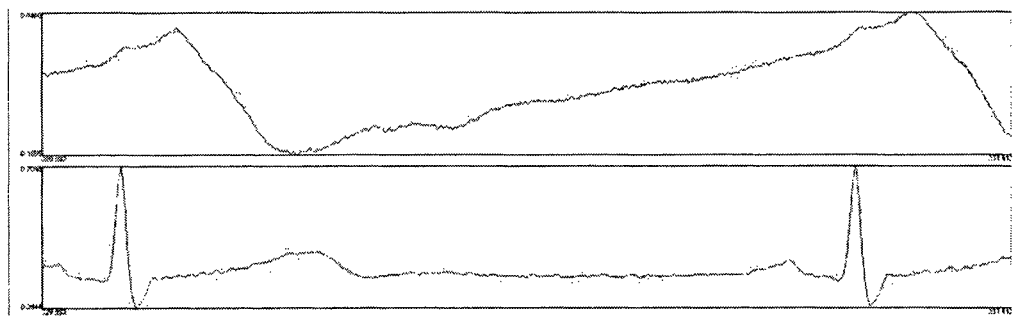

FIG. 3 shows a schematic example of the derivative of the voltage plethysmogram, indicating the Left Ventricular Ejection Time (LVET). FIG. 4 shows a recording using the graphical user interface (GUI) of the invention showing the VP, while FIG. 5 shows the VP and the ECG using the GUI of the invention.

The complete processing system of the present invention for the CO part consists of 2 ANFIS models.

Figure 7:
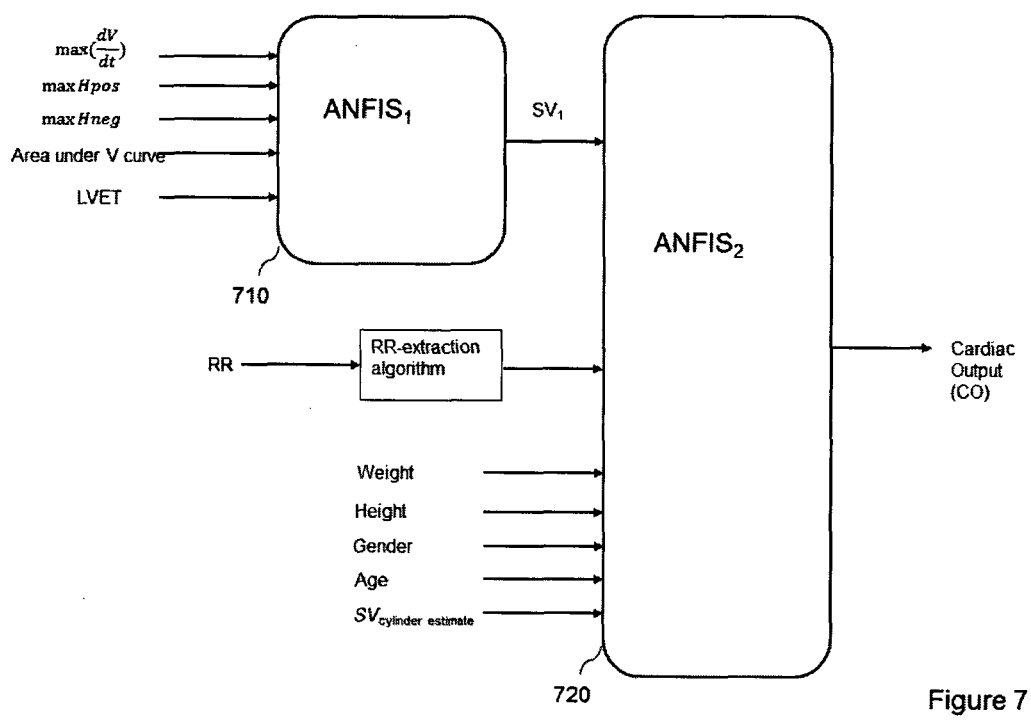

ANFIS1 (710) takes as input the parameters extracted from the voltage plethysmogram, in a preferred embodiment there are at least 3 inputs, as shown in FIG. 7, however more inputs could be included. As input for ANFIS2 (720) is also used a simple estimate of SV, termed SV cylinder estimate $$SV \text{ cylinder estimate} = kL^2 \max\left(\frac{dV}{dt}\right) t_c$$

where L is length of the trunk (could be the distance between the lower and upper pair of electrodes) and max (dV/dt) is the maximum of the derivative of the voltage plethysmogram. The constant, k, adjusts the SV to the normal range which is 50 to 150 ml.

The RR interval is an input to ANFIS 2 as well. The RR is the reciprocal of the HR hence CO can be calculated as $$CO = SV/RR.$$

The range of CO is 0 to 25 l/min, while the normal physiological range is 4 to 8 l/min. Finally, gender and age are added as well as input to ANFIS2. The output of ANFIS2 is the final estimate of cardiac output (CO). The training of the ANFIS models is carried out with a large amount of data where the CO is known for the patient. The training defines the parameters of the ANFIS model which can then predict CO when the input are presented to the model. The output of the ANFIS model defines the CO.

Background of the Inflammation Index.

The works of Tracey (Tracey, K. Understanding immunity requires more than immunology. Nat. Immunol. 2010; 11, 561-564.) have clearly defined the role of the vagus nerve as the afferent sensor from the point of aggression to the brain, and perhaps more important from a therapeutic point of view, in the efferent pathway of this reflex because its stimulation facilitate the process of the intensity of the inflammation. The vagus nerve, the tenth cranial nerve, carry the fibers of the neural pathways of the parasympathetic system branching out and reaching virtually every organ. Details of the alterations induced by the inflammatory response were published by (Huston J M, Tracey K J. The pulse of inflammation: heart rate variability, the cholinergic anti-inflammatory pathway and implications for therapy. J Intern Med. 2011 January; 269(1):45-53.).

The cholinergic anti-inflammatory pathway descends on the vagus nerve. The vagal stimulation of the heart leads to changes in heart rate variability (HRV). The study or HRV using mathematical techniques such as spectral analysis allowed to identify the frequencies that are associated with increased specificity to changes due to parasympathetic dominance, possibly with an estimate of vagal cholinergic activity by analyzing the rapid frequency component of HRV according to the ESC Task Force, 1996.

Mechanisms of inflammation induce changes in behavior and body constituting inflammatory syndrome associated with illness. Initially and under control, inflammation promotes healing through the molecular and cellular. But when not properly compensated, the inflammation can have serious consequences for the patient. The inflammatory cascade can be very aggressive towards the patient's own tissue leading to sepsis, even death (Tracey K, Nat Immunol, 2010).

In the case of the surgical aggression and neuroinflammation produced, lack of compensation perpetuate inflammatory neuronal involvement leading to cognitive impairment in the medium term as already demonstrated in experimental animal studies. This hypothesis could justify the high percentage of cognitive alterations detected with no apparent relation to other etiologies beyond increased incidence of higher age.

The patent application PCT/IB2013/054615 "METHOD AND SYSTEM FOR ASSESSING LIKELIHOOD OF SEPSIS" discloses a system for detection of sepsis, however the present invention differs by using ANFIS models for combining the parameters. The disclosed system PCT/IB2013/054615 uses a radio frequency input which is not used in the present invention.

The patent application PCT/CA2012/000243 "METHOD AND SYSTEM FOR DETERMINING HRV AND RRV AND USE TO IDENTIFY POTENTIAL CONDITION ONSET" discloses a system using HRV and respiratory rate variability (RRV) for detection of sepsis, though in infant patients, but it does not use an ANFIS model as done in the present invention.

The US patent application no 20050137484 "Method and apparatus for the early diagnosis of subacute, potentially catastrophic illness" is intended to be used on infants and newborns, and as such does not cover the complete age range as the present invention does and it does not use an ANFIS model as is done in the present application.

The US patent application US7941199 B2, disclose a method for the assessment of sepsis, but it does not use Heart Rate Variability nor ANFIS, hence the present invention differs significantly.

The US patent application US 20110137852 A1, "Sepsis Monitoring and Control" does include the usage of Heart Rate but not heart rate variability nor ANFIS, hence the present invention is substantially different.

Description of the Invention for the Calculation of the Inflammation Index.

The second objective of the present invention is to monitor the degree of inflammation, typically but not necessarily, of critically ill patients in the intensive care unit, by analyzing the heart rate variability and compensating these changes for the influence of the depth of anaesthesia as assessed by for example the qCON hypnotic effect index derived from the electroencephalogram (EEG).

The present invention records the electrocardiogram (ECG), extracts the R-R interval and other features from the ECG, such as intervals between p,q,r and t peaks. Furthermore an FFT of the RR interval is carried out, from which the Heart Rate Variability (HRV) is defined. From the HRV, different frequency bands are extracted for example HF and LF, see table 1.

Other parameters are extracted as well, such as RMSSD, SDSD, PNN50 as described in table 1.

Figure 9:
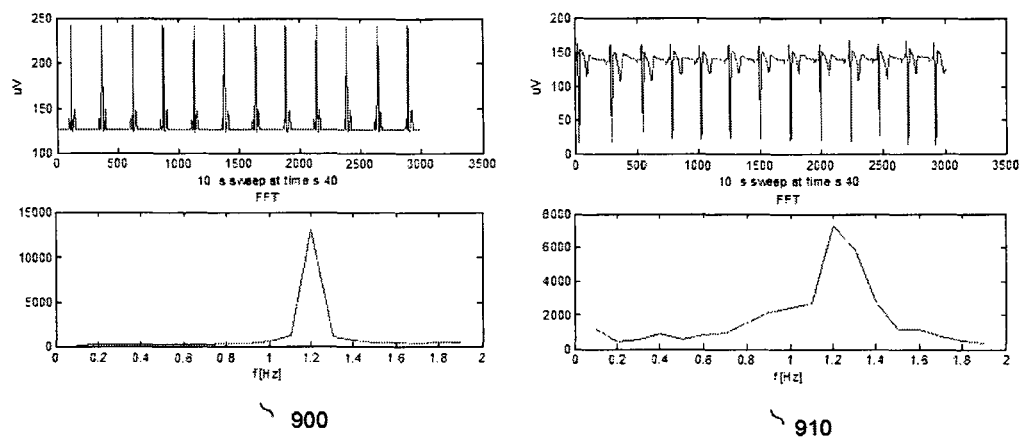

An FFT is carried out directly on the ECG from which the overall variation of the heart rate can be detected in the spectrum. This is shown in FIG. 9 where the spectrum to the right (910) from an awake and healthy subject is much wider than the spectrum to the left (900), which is from a simulated ECG.

Figure 8:
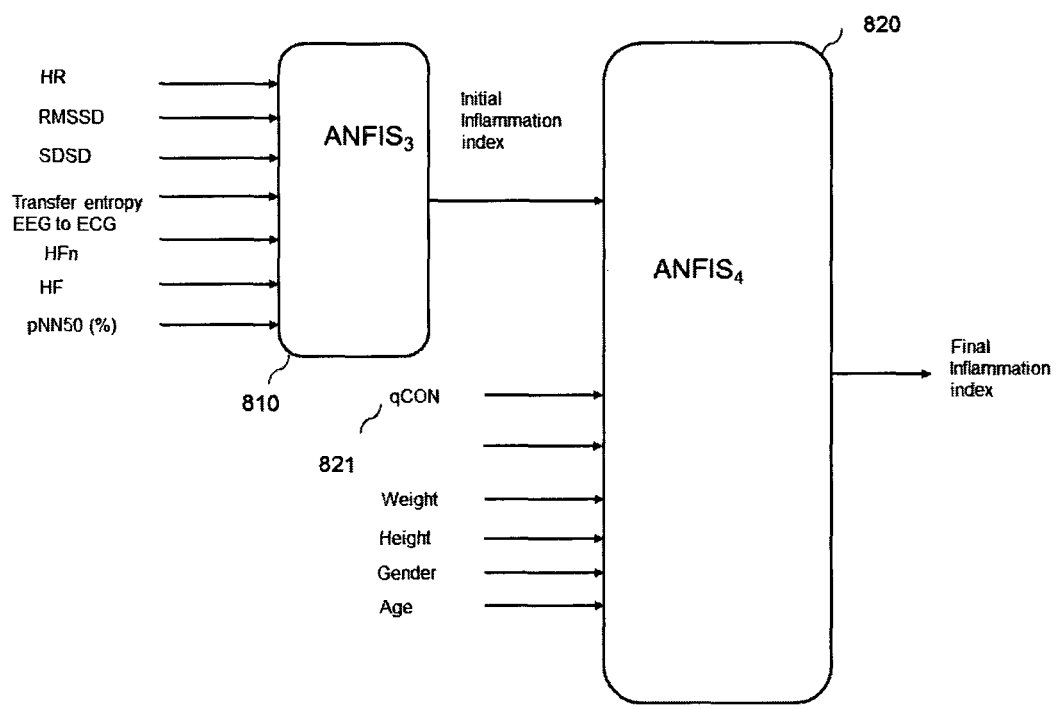

As shown in FIG. 8, the parameters derived from the ECG are fed into an ANFIS model (810) and in a second step they are combined with demographic data and the qCON (820) in order to define the final index of inflammation.

A novelty of this index is that the EEG derived index, the qCON, is used in the model to compensate for the fact that HRV is typically affected by the level of consciousness of the patient during sedation. HRV is typically decreased as an effect of the anaesthesia, but as the depth of anaesthesia is known from the value of the qCON, both the qCON and the initial inflammation index is fed into the ANFIS 4 model, where a fuzzy rule will be automatically generated in a such way that the final inflammation index is compensated for the depth of anaesthesia.

Another novelty of the invention is the application of transfer entropy from EEG to ECG. Symbolic transfer entropy measures the causal influence of source signal X on target signal Y, and is based on information theory. Here the EEG equal X while ECG equals Y. The information transfer from signal X to Y is measured by the difference of two mutual information values, I [YF; XP, YP] and I [YF; YP], where XP, YP, and YF are, respectively, the past of source and target signals and the future of the target signal. The difference corresponds to information transferred from the past of source signal XP to the future of the target signal YF and not from the past of the target signal itself. The article "Vicente R, Wibral M, Lindner M, Pipa G: Transfer entropy—A model-free measure of effective connectivity for the neurosciences. J Comput Neurosci 2011; 30:45-67" is incorporated here as a reference. The transfer entropy EEG to ECG is fed into the ANFIS3 (810) model which defines the initial inflammation index.

In a preferred embodiment the transfer entropy from EEG to ECG, is calculated from the frequency with the highest energy content in FFT spectrum of the EEG to the HF of the RR-interval from the ECG.

Figure 10:
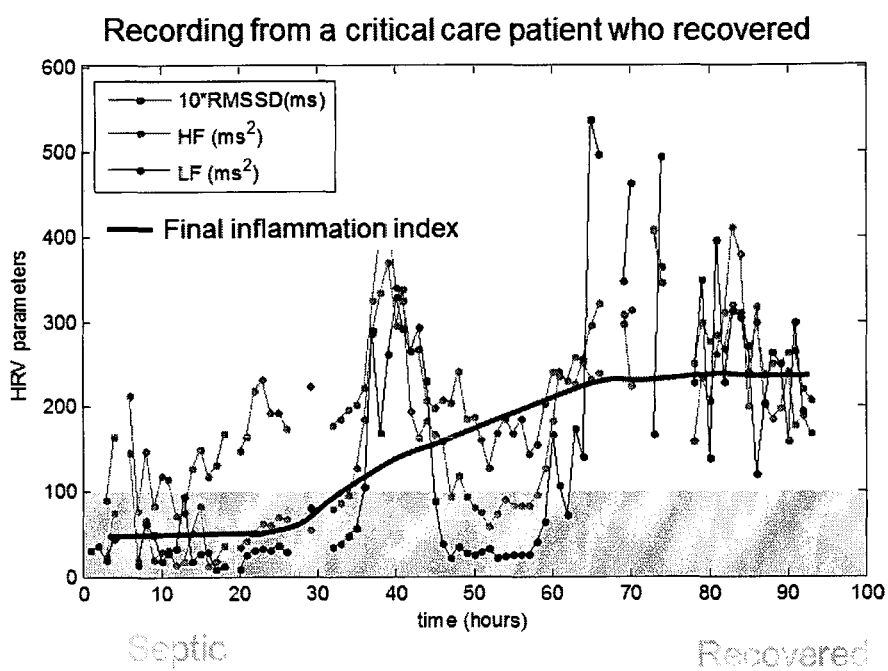

The output of ANFIS4 (820) is the final inflammation index, which is low, below 50, when the patient is septic and high, above 200, when the patient has recovered as shown in FIG. 10. The range of the final inflammation index is 0 to 300 while the index is unitless.

LEGEND TO FIGURES

FIG. 1. The complete system for the assessment of the cardiac output and the final inflammation index FIG. 2 Schematic voltage plethysmogram FIG. 3 Schematic first derivative of the voltage plethysmogram FIG. 4 Example of a recording of a voltage plethysmogram FIG. 5 Example of voltage plethysmogram and ECG FIG. 6 Structure of a Sugeno type Adaptive Neuro Fuzzy Inference System (ANFIS)

FIG. 7 The digital signal processing approach containing 2 ANFIS models for the assessment of the cardiac output FIG. 8 The digital signal processing approach containing 2 ANFIS models for the assessment of the inflammation index FIG. 9 An example of the variation in the heart rate from a simulated signal (900) and from an awake healthy subject (910)

FIG. 10 An example of the behavior of frequency parameters extracted from the HRV and the final inflammation index

The invention claimed is:

1. An apparatus for determining systemic inflammation in a subject; said apparatus comprises:
   a. at least one sensor for receiving electroencephalogram (EEG) data and at least one sensor for receiving electrocardiogram (ECG) data;

b. at least one processor; and, c. at least one non-transitory computer readable medium coupled to said at least one processor, said at least one non-transitory computer readable medium comprises an operation executed by said at least one processor, said operation is calculating root mean square differences between successive RR intervals (RMSSDI) from said ECG data, high frequency (HF) from said ECG data, and transfer entropy between said EEG data and said ECG data;

wherein said at least one non-transitory computer readable medium additionally comprises an operation of combining said RMSSD, HF, and transfer entropy by an adaptive neuro fuzzy inference system (ANFIS) into an initial index of systemic inflammation an operation of extracting qCON hypnotic effect index from said EEG data, an operation of correcting said initial index of systemic inflammation by said qCON hypnotic effect index to give a final index of systemic inflammation, and an operation of outputting the final index of systemic inflammation.

2. The apparatus according to claim 1, wherein the at least one sensor for receiving EEG data consists of at least 3 electrodes, wherein said at least 3 electrodes are positioned on a forehead of said subject.

3. The apparatus according to claim 1, wherein the at least one sensor for receiving ECG data consists of at least two electrodes, wherein said at least two electrodes are positioned on a thorax of said subject.

4. The apparatus according to claim 1, wherein said transfer entropy between said EEG data and ECG data is calculated by a symbolic transfer entropy from said EEG data to said ECG data via a vagal nerve.

5. The apparatus according to claim 1 wherein the operation of correcting comprises combining said initial index of system inflammation and said qCON hypnotic effect index by another adaptive neuro fuzzy inference system (ANFIS) to give said final index of systemic inflammation.

6. The apparatus according to claim 1 wherein the operation of outputting the final index of systemic inflammation comprises displaying the final index of inflammation.

7. An apparatus for determining stroke volume in a subject; said apparatus comprises:

a. (i) at least one sensor for receiving electroencephalogram (EEG) data, and (ii) at least one sensor for receiving electroacardiogram (ECG) data and voltage curve data generated by a constant current generator for each heart-beat of a subject;

b. at least one processor; and, c. at least one non-transitory computer readable medium coupled to said at least one processor, said at least one non-transitory computer readable medium comprises an operation executed by said at least one processor, said operation is calculating an area under said voltage curve for each heart-beat, a derivative of said voltage curve, maxHpos from said voltage curve, and maxHneg from said voltage curve;

wherein said at least one non-transitory computer readable medium additionally comprises an operation of combining said area under said voltage curve for each heart-beat, said derivative of said voltage curve, said maxHpos from said voltage curve, and said maxHneg from said voltage curve, by an adaptive neuro fuzzy inference system (ANFIS) into a final index of stroke volume; and an operation of outputting the final index of stroke volume.

8. The apparatus according to claim 7 wherein the operation of outputting the final index of stroke volume comprises displaying the final index of stroke volume.

9. An apparatus for determining cardiac output in a subject; said apparatus comprises:

a. (i) at least one sensor for receiving electroencephalogram (EEG) data, and (ii) at least one sensor for receiving electroacardiogram (ECG) data and voltage curve data generated by a constant current generator for each heart-beat of a subject;

b. at least one processor; and, c. at least one non-transitory computer readable medium coupled to said at least one processor, said at least one non-transitory computer readable medium comprises an operation executed by said at least one processor, said operation is calculating stroke volume, and heart rate from said ECG data or time between successive R-peaks in the ECG data (RR interval);

wherein said at least one non-transitory computer readable medium additionally comprises an operation of combining said stroke volume and said heart rate from said ECG data or said time between successive R-peaks in the ECG data (RR interval), by an adaptive neuro fuzzy inference system (ANFIS) into a final index of cardiac output;

and an operation of outputting the final index of cardiac output.

10. The apparatus according to claim 9 wherein the operation of outputting the final index of cardiac output comprises displaying the final index of cardiac output.

11. The apparatus according to claim 7, wherein the at least one sensor for receiving electrocardiogram (ECG) data and voltage curve data receives voltage curve data and comprises at least two electrodes, and wherein said at least two electrodes are positioned on a thorax of said subject.

12. The apparatus according to claim 7, wherein the at least one sensor for receiving electrocardiogram (ECG) data and voltage curve data receives electrocardiogram (ECG) data and voltage curve data with electrodes that are the same electrodes for receiving both said electrocardiogram (ECG) data and said voltage curve data.

13. The apparatus according to claim 9, wherein the at least one sensor for receiving ECG data and voltage curve data receives ECG data and comprises at least two electrodes, and wherein said at least two electrodes are positioned on a thorax of said subject.

* * * * *